(12) United States Patent
Asada et al.

(10) Patent No.: US 9,873,098 B2
(45) Date of Patent: Jan. 23, 2018

(54) THREE-COMPONENT MIXING APPARATUS AND THREE-COMPONENT MIXING ADHESIVE KIT

(71) Applicant: MITSUI CHEMICALS, INC., Minato-ku (JP)

(72) Inventors: Noriaki Asada, Mobara (JP); Kenju Sasaki, Omuta (JP); Shinya Aoki, Yokohama (JP); Kazuya Sakata, Ichihara (JP); Hiroshi Naruse, Chiba (JP)

(73) Assignee: MITSUI CHEMICALS, INC., Tokyo (JP)

( * ) Notice: Subject to any disclaimer, the term of this patent is extended or adjusted under 35 U.S.C. 154(b) by 29 days.

(21) Appl. No.: 14/399,111

(22) PCT Filed: Apr. 25, 2013

(86) PCT No.: PCT/JP2013/062257
§ 371 (c)(1),
(2) Date: Nov. 5, 2014

(87) PCT Pub. No.: WO2013/179832
PCT Pub. Date: Dec. 5, 2013

(65) Prior Publication Data
US 2015/0117140 A1    Apr. 30, 2015

(30) Foreign Application Priority Data

May 30, 2012 (JP) ................................. 2012-123322

(51) Int. Cl.
*B01F 15/02* (2006.01)
*B01F 13/00* (2006.01)
(Continued)

(52) U.S. Cl.
CPC .... *B01F 15/0237* (2013.01); *A61B 17/00491* (2013.01); *B01F 3/12* (2013.01);
(Continued)

(58) Field of Classification Search
CPC .................................................. B01F 15/0237
(Continued)

(56) References Cited

U.S. PATENT DOCUMENTS 3,932,136 A * 1/1976 Stickney ............... B01F 5/0077
141/105
5,304,165 A     4/1994 Haber et al.
(Continued)

FOREIGN PATENT DOCUMENTS

CN          1077112       10/1993
CN       102170851 A       8/2011
(Continued)

OTHER PUBLICATIONS

International Search Report (PCT/ISA/210) dated Aug. 6, 2013, by the Japanese Patent Office as the International Searching Authority for International Application No. PCT/JP2013/062257.
(Continued)

*Primary Examiner* — Abbas Rashid
(74) *Attorney, Agent, or Firm* — Buchanan, Ingersoll & Rooney PC

(57) ABSTRACT

A three-component mixing apparatus and a three-component mixing adhesive kit, which allow anyone to easily and uniformly mix three kinds of drugs in mixing a three-component adhesive used in, e.g., surgical procedure (or treatment) or dental procedure (or treatment), includes a syringe filled with a first drug; a plunger; and an infusion-needle connector having a connecting part for a second drug container and a connecting part for a third drug container and a confluent path formed on a base end part. The first
(Continued)

drug, the second drug and the third drug are mixed in the syringe by removably attaching the infusion-needle connector to a discharge opening of the syringe, the second drug container to its connecting part and the third drug container to its connecting part and then pulling the plunger inserted into the syringe to introduce the second drug and the third drug into the syringe.

8 Claims, 14 Drawing Sheets

(51) Int. Cl.
    *A61B 17/00*     (2006.01)
    *B01F 3/12*     (2006.01)

(52) U.S. Cl.
    CPC ...... *B01F 13/0023* (2013.01); *B01F 15/0206* (2013.01); *B01F 15/0225* (2013.01); *B01F 15/0258* (2013.01); *A61B 2017/00495* (2013.01); *B01F 2215/0027* (2013.01); *B01F 2215/0032* (2013.01)

(58) Field of Classification Search
    USPC ..... 366/130, 153.2, 163.1, 176.3–176.4, 189
    See application file for complete search history.

(56) References Cited

U.S. PATENT DOCUMENTS

| | | | |
|---|---|---|---|
| 5,620,427 A * | 4/1997 | Werschmidt | A61M 39/10 137/516.13 |
| 5,697,524 A * | 12/1997 | Sedlmeier | B01F 13/002 222/105 |
| 5,957,166 A * | 9/1999 | Safabash | B01F 11/0082 141/100 |
| 6,062,722 A * | 5/2000 | Lake | B01F 5/0615 366/130 |
| 6,152,913 A * | 11/2000 | Feith | A61M 39/10 604/533 |
| 6,162,200 A * | 12/2000 | Sawa | A61M 5/31513 604/218 |
| 6,254,269 B1 | 7/2001 | Ernstson et al. | |
| 6,302,574 B1 * | 10/2001 | Chan | A61B 17/8825 222/137 |
| 6,402,364 B1 * | 6/2002 | Esclar | A45D 19/02 222/135 |
| 6,494,865 B1 | 12/2002 | Alchas | |
| 6,612,465 B2 * | 9/2003 | Pierson | A61O 5/062 222/137 |
| 7,135,027 B2 * | 11/2006 | Delmotte | A61B 17/8816 606/92 |
| 7,635,344 B2 | 12/2009 | Tennican et al. | |
| 7,731,678 B2 | 6/2010 | Tennican et al. | |
| 7,731,679 B2 | 6/2010 | Tennican et al. | |
| 7,749,189 B2 | 7/2010 | Tennican et al. | |
| 7,753,891 B2 | 7/2010 | Tennican et al. | |
| 7,776,011 B2 | 8/2010 | Tennican et al. | |
| 7,985,211 B2 | 7/2011 | Tennican et al. | |
| 8,231,567 B2 | 7/2012 | Tennican et al. | |
| 8,376,188 B2 | 2/2013 | Riera | |
| 8,529,502 B2 | 9/2013 | Radmer | |
| 9,056,288 B2 * | 6/2015 | Greter | B01F 5/061 |
| 2004/0068266 A1 | 4/2004 | Delmotte | |
| 2006/0079834 A1 | 4/2006 | Tennican et al. | |
| 2007/0012724 A1 | 1/2007 | Feinberg et al. | |
| 2007/0249996 A1 | 10/2007 | Tennican et al. | |
| 2007/0255203 A1 | 11/2007 | Tennican et al. | |
| 2007/0255226 A1 | 11/2007 | Tennican et al. | |
| 2007/0260176 A1 | 11/2007 | Tennican et al. | |
| 2007/0265574 A1 | 11/2007 | Tennican et al. | |
| 2007/0265578 A1 | 11/2007 | Tennican et al. | |
| 2007/0276322 A1 | 11/2007 | Tennican et al. | |
| 2008/0316855 A1 | 12/2008 | Ferrante et al. | |
| 2009/0099547 A1 | 4/2009 | Radmer | |
| 2011/0230856 A1 | 9/2011 | Kyle et al. | |
| 2012/0067429 A1 | 3/2012 | Mosler et al. | |
| 2012/0104044 A1 * | 5/2012 | Pappalardo | B05C 17/005 222/137 |
| 2012/0279884 A1 | 11/2012 | Tennican et al. | |
| 2012/0302986 A1 | 11/2012 | Brem et al. | |
| 2013/0272085 A1 * | 10/2013 | Quinto | B29C 47/12 366/76.7 |
| 2013/0313281 A1 * | 11/2013 | Kane | B65D 83/0033 222/1 |

FOREIGN PATENT DOCUMENTS

| | | | |
|---|---|---|---|
| CN | 203280431 U | 11/2013 | |
| EP | 0 928 182 B1 | 7/1999 | |
| EP | 0869826 B1 * | 10/2003 | ............ A61M 39/10 |
| EP | 2 283 885 A1 | 2/2011 | |
| JP | 7-136264 A | 5/1995 | |
| JP | 2006-230467 A | 9/2006 | |
| JP | 2009-534144 A | 9/2009 | |
| JP | 2012-500659 A | 1/2012 | |
| KR | 10-1018515 B1 | 3/2011 | |
| RU | 2 181 620 C2 | 4/2002 | |
| RU | 2 481 858 C2 | 5/2013 | |
| SU | 244228 A1 | 11/1969 | |
| TW | 200626197 | 8/2006 | |
| WO | WO 93/011709 A1 | 6/1993 | |
| WO | WO 97/25015 A1 | 7/1997 | |
| WO | WO 2004/108060 A1 | 12/2004 | |
| WO | WO 2006/058153 A1 | 6/2006 | |
| WO | WO 2010/120953 A2 | 10/2010 | |
| WO | WO 2011/059823 A1 | 5/2011 | |
| WO | WO 2011/091542 A1 | 8/2011 | |

OTHER PUBLICATIONS

Office Action dated Nov. 6, 2015, issued by the Russian Patent Office in corresponding Russian Patent Application No. 2014152856/05 with an English Translation of the Office Action (4 pages).

Office Action dated Dec. 8, 2015, issued by the Japanese Patent Office in corresponding Japanese Patent Application No. 2014-518354 (2 pages).

Extended European Search Report dated Dec. 18, 2015, issued by the European Patent Office in corresponding European Patent Application No. 13797259.2 (8 pages).

Office Action issued in corresponding Chinese Application No. 201310216363.4 dated Feb. 28, 2015 (7 pages).

Office Action issued by the Korean Patent Office in corresponding Korean Patent Application No. 10-2014-7030102 dated Jan. 22, 2016 (6 pages).

Office Action issued by the Taiwanese Patent Office in corresponding Taiwanese Patent Application No. 102116583 dated Sep. 23, 2016 (5 pages).

\* cited by examiner

[Fig. 1]
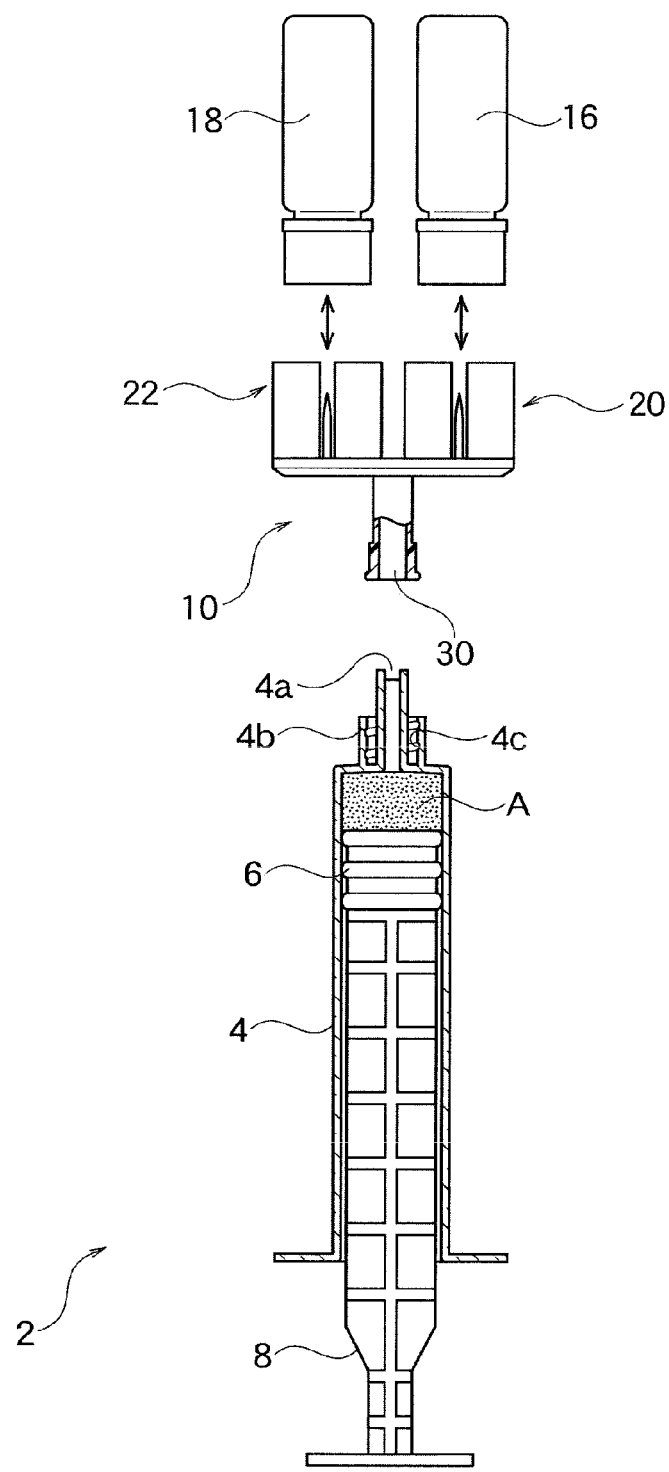

[Fig. 2]
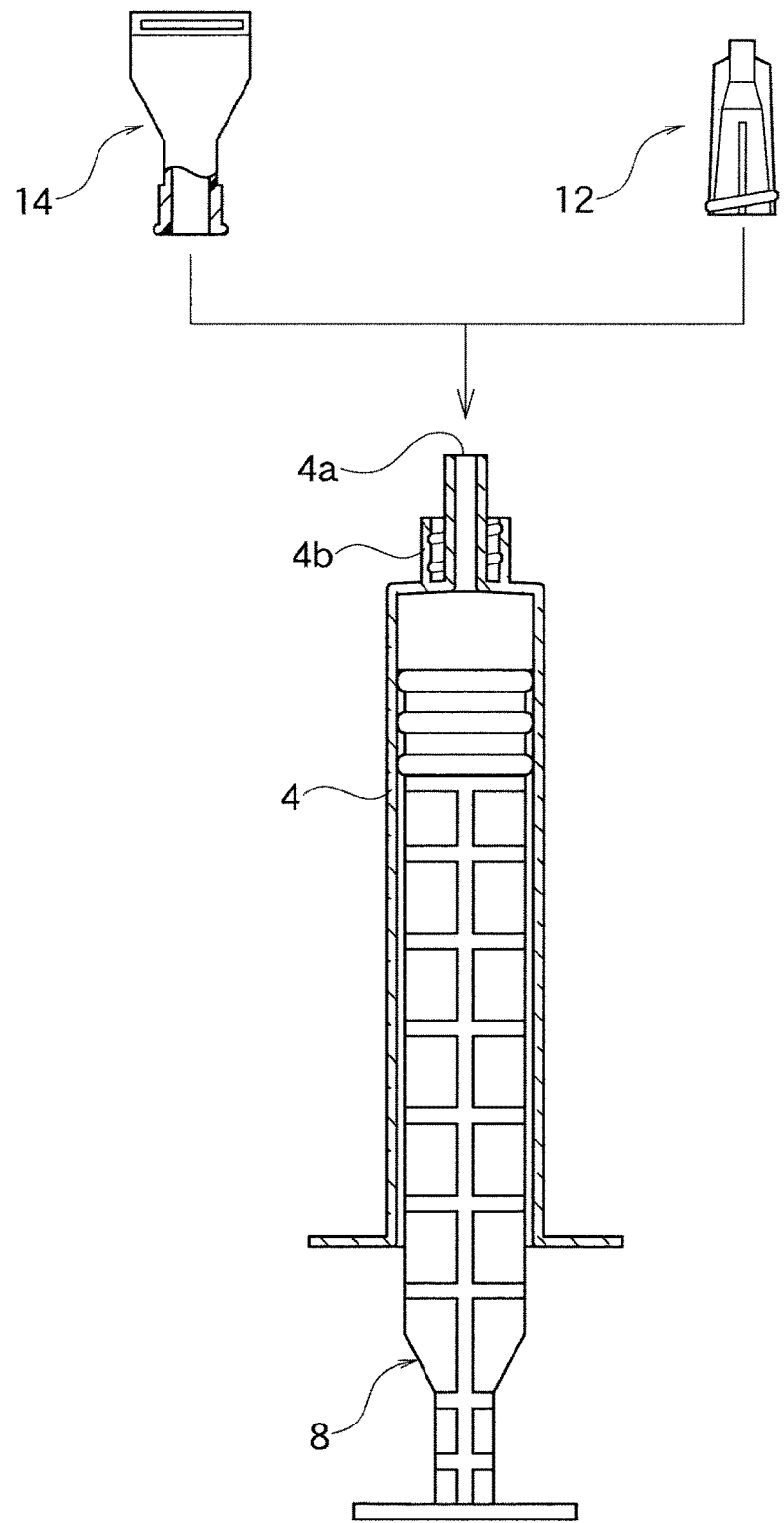

[Fig. 3]
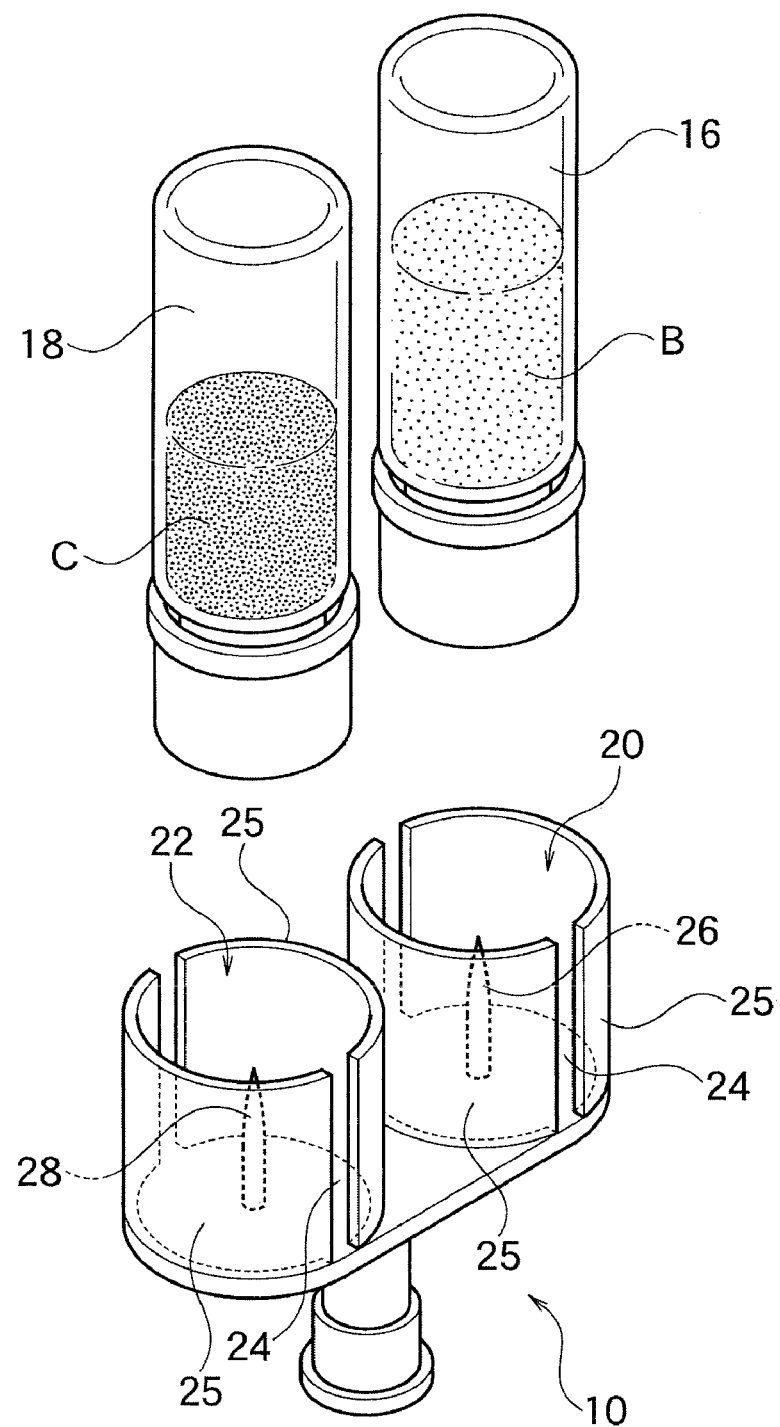

[Fig. 4]
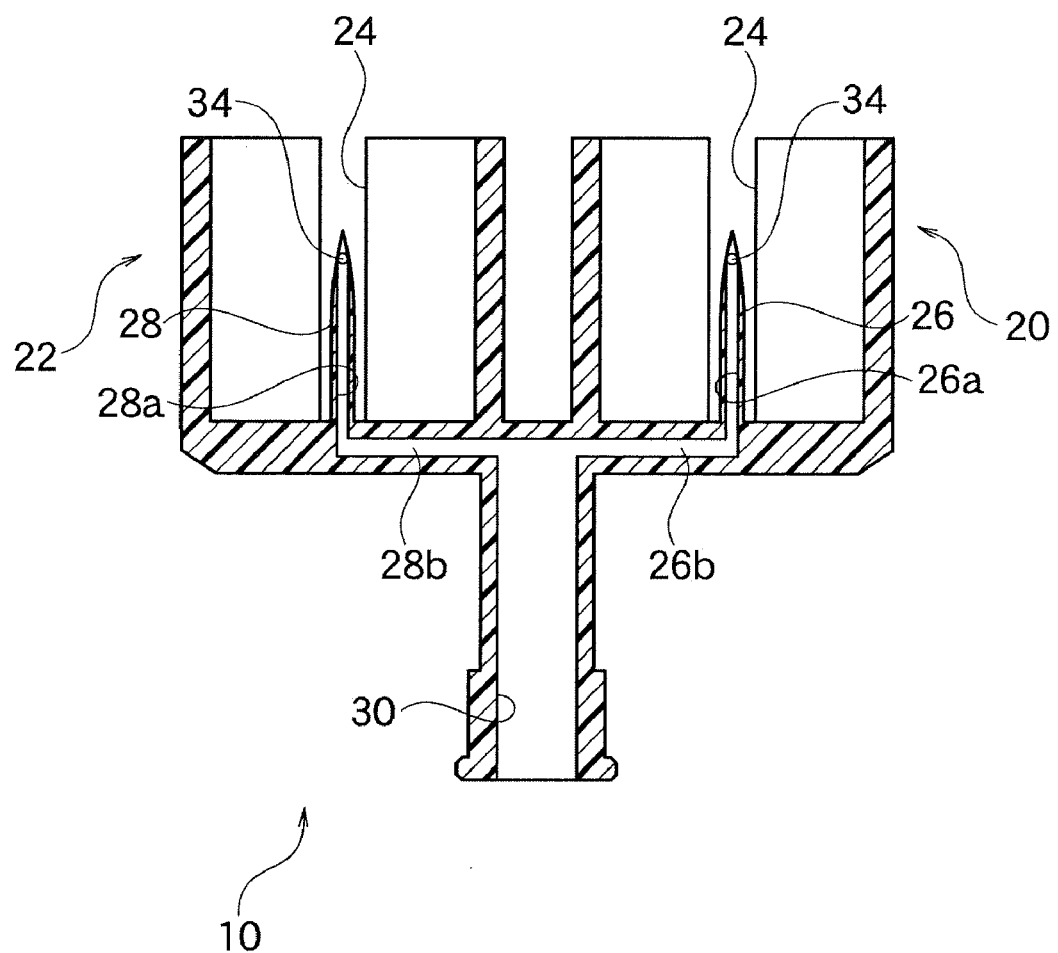

[Fig. 5]
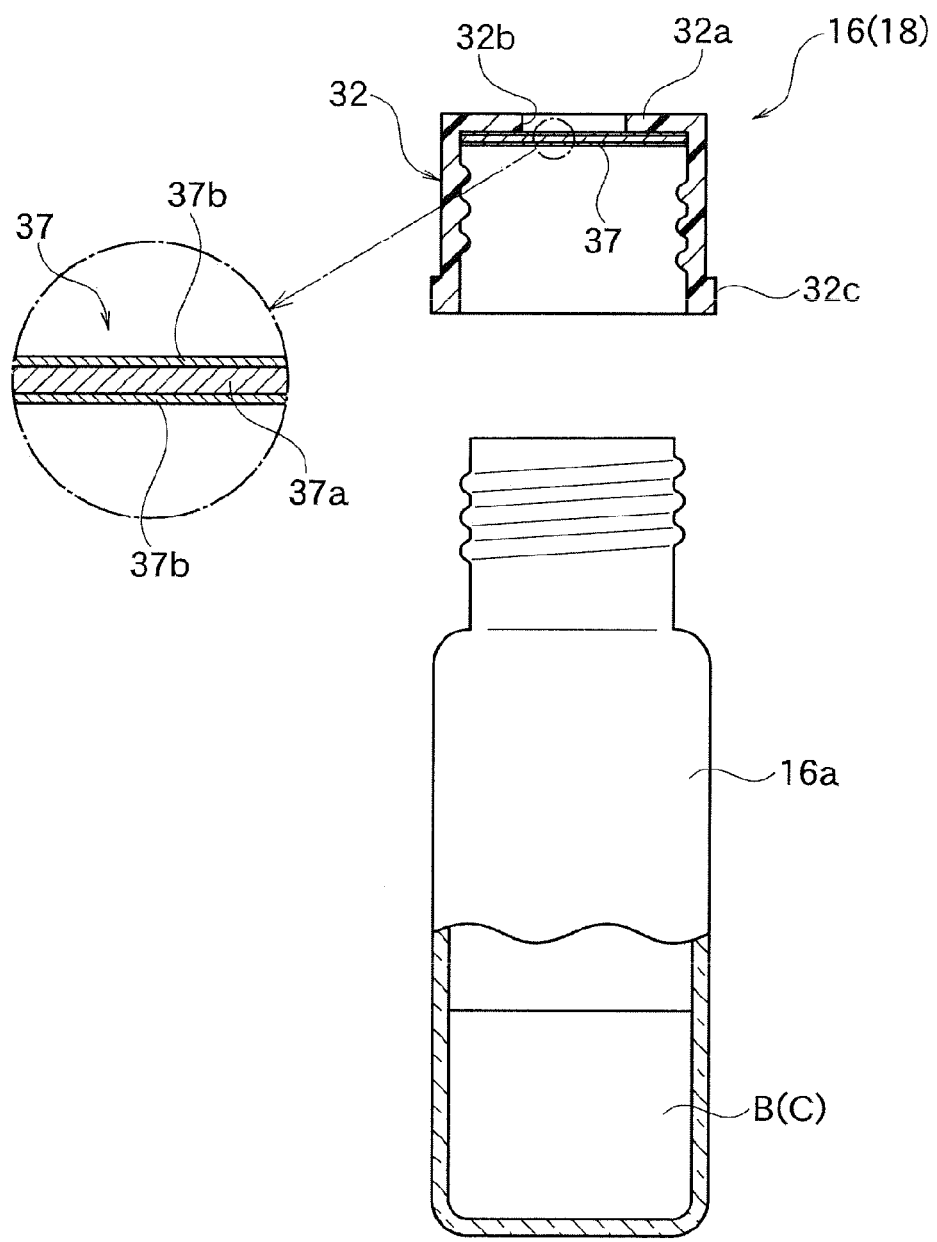

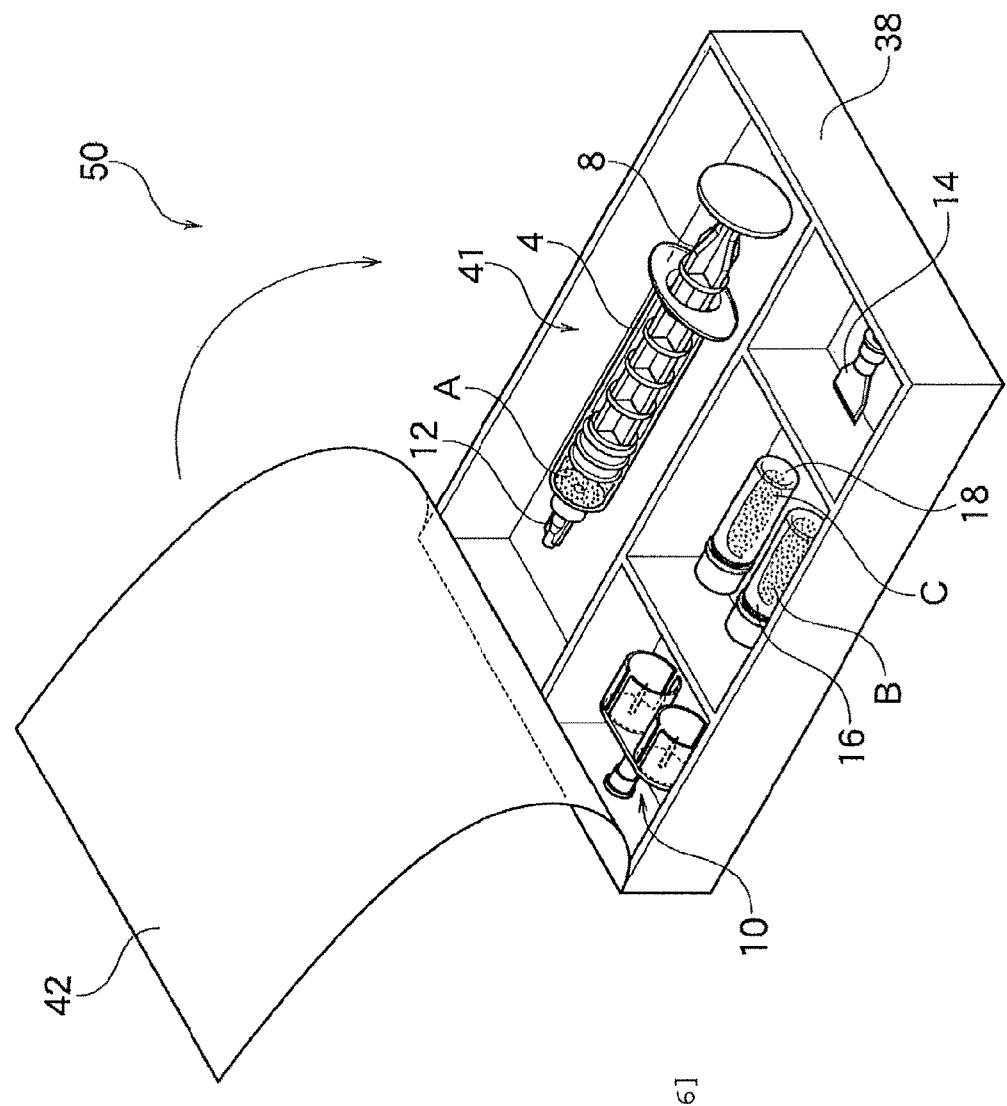
[Fig. 6]

[Fig. 7]
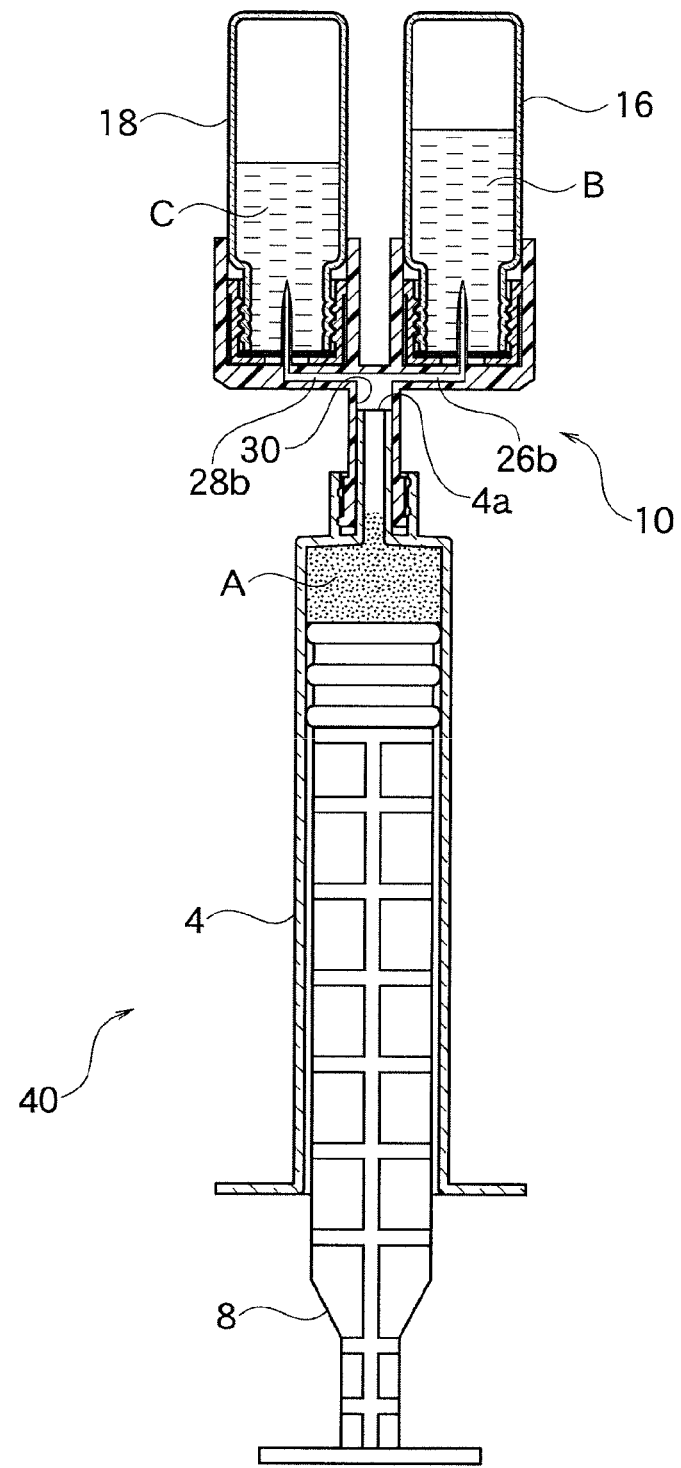

[Fig. 8]
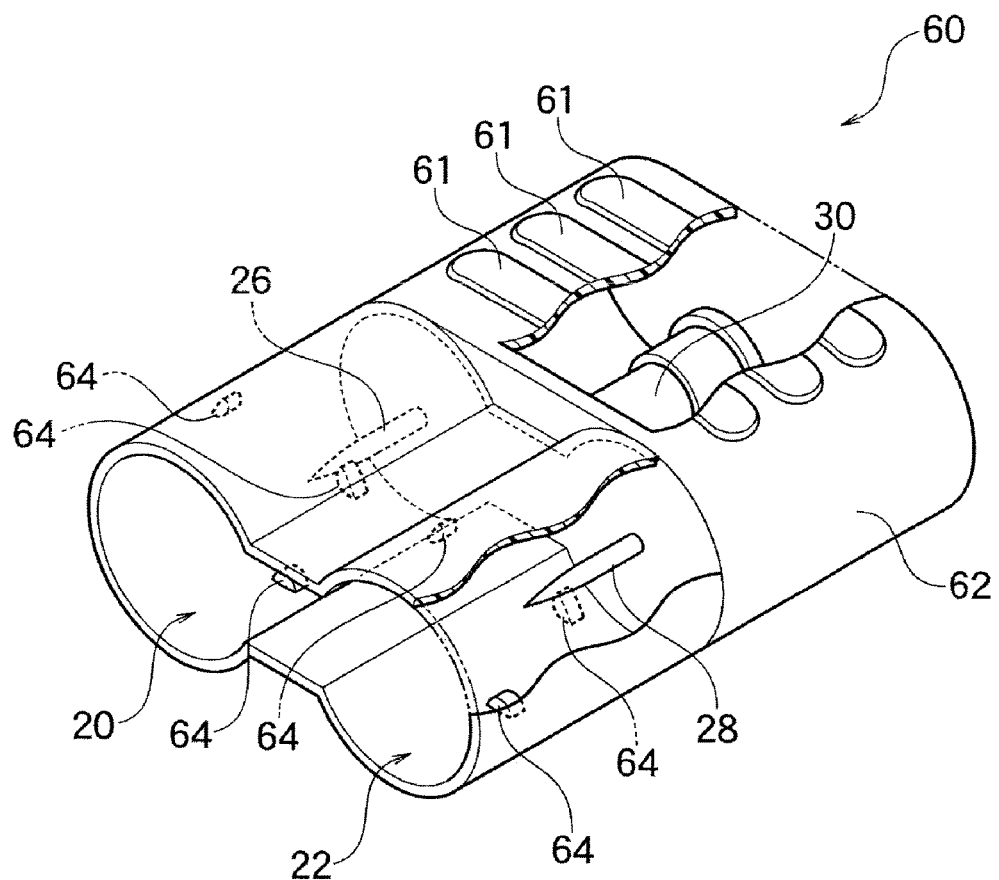

[Fig. 9]
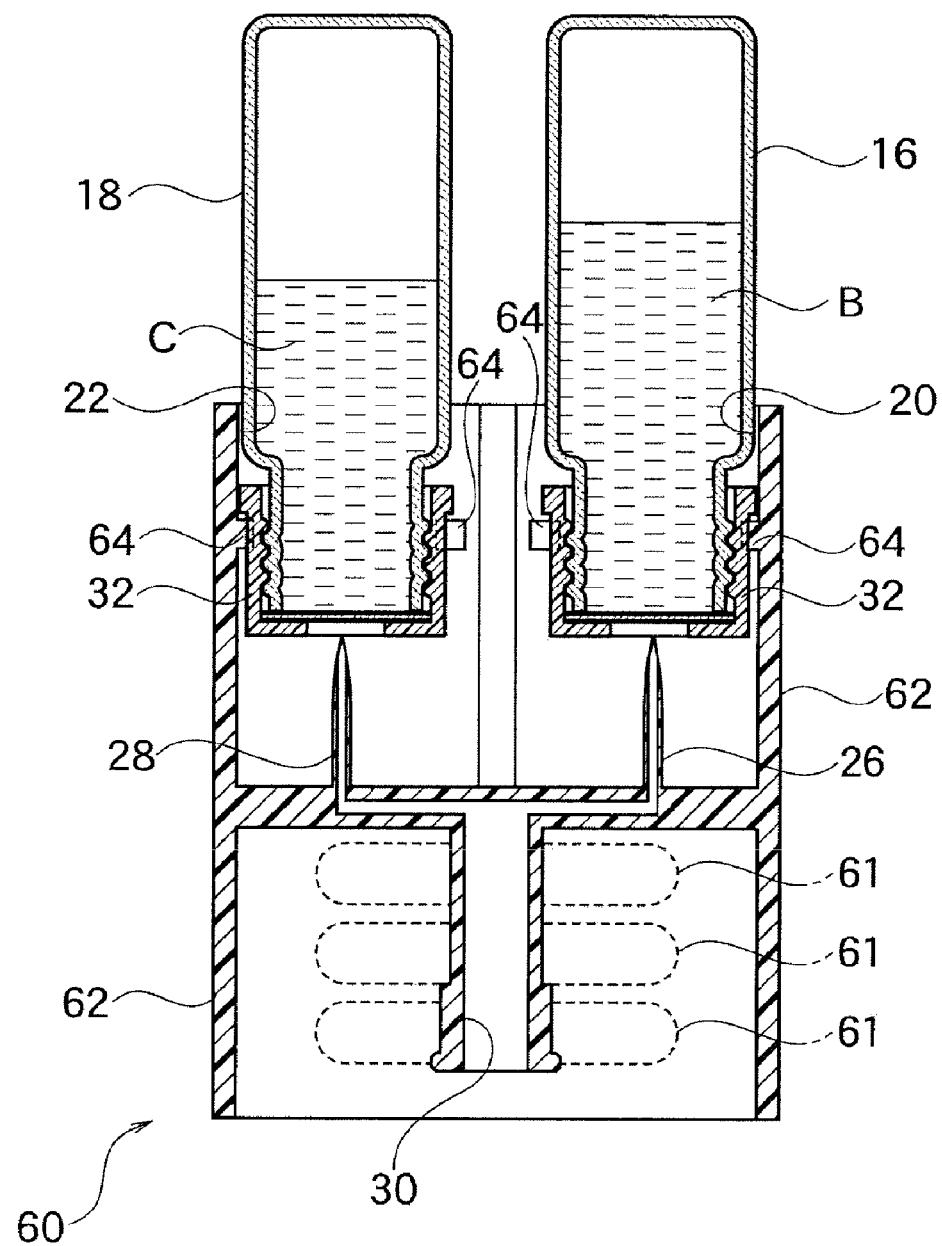

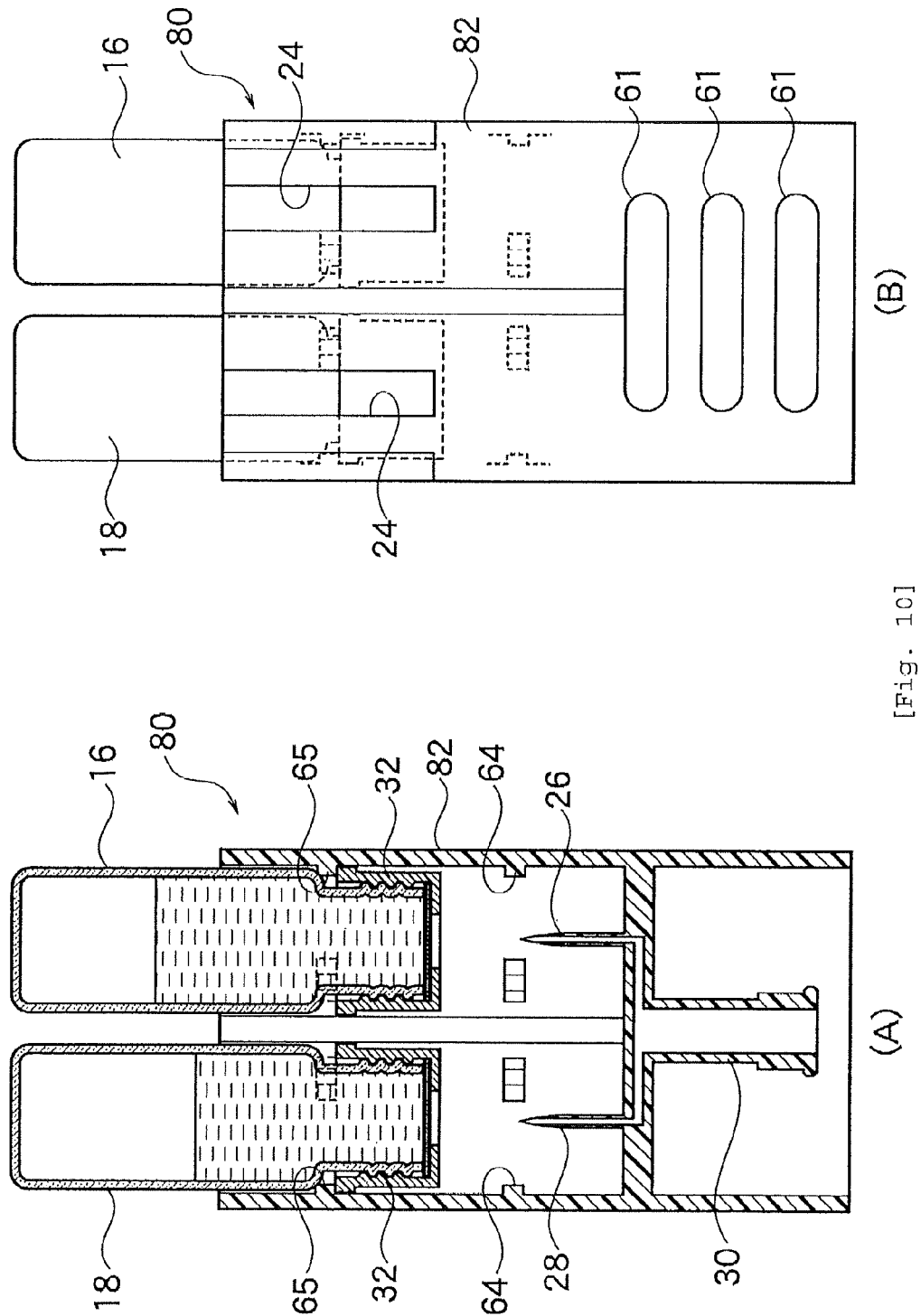

[Fig. 11]
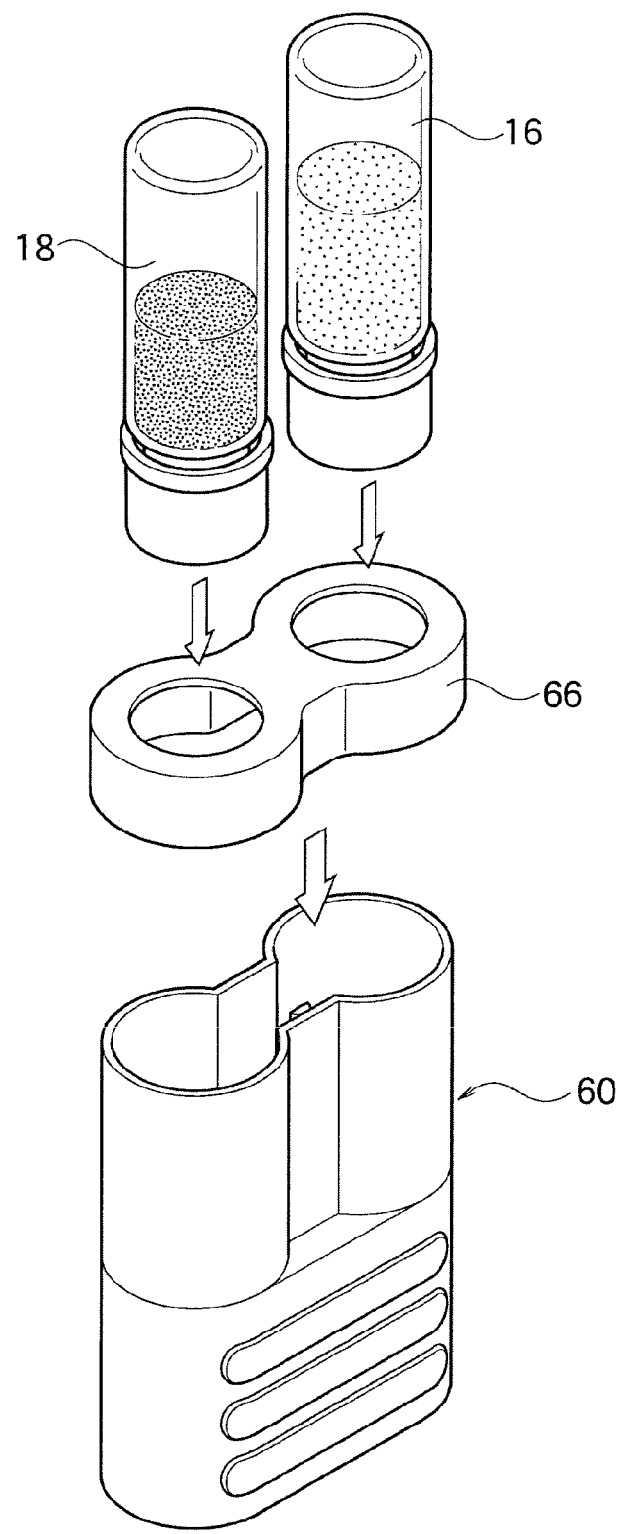

[Fig. 12]
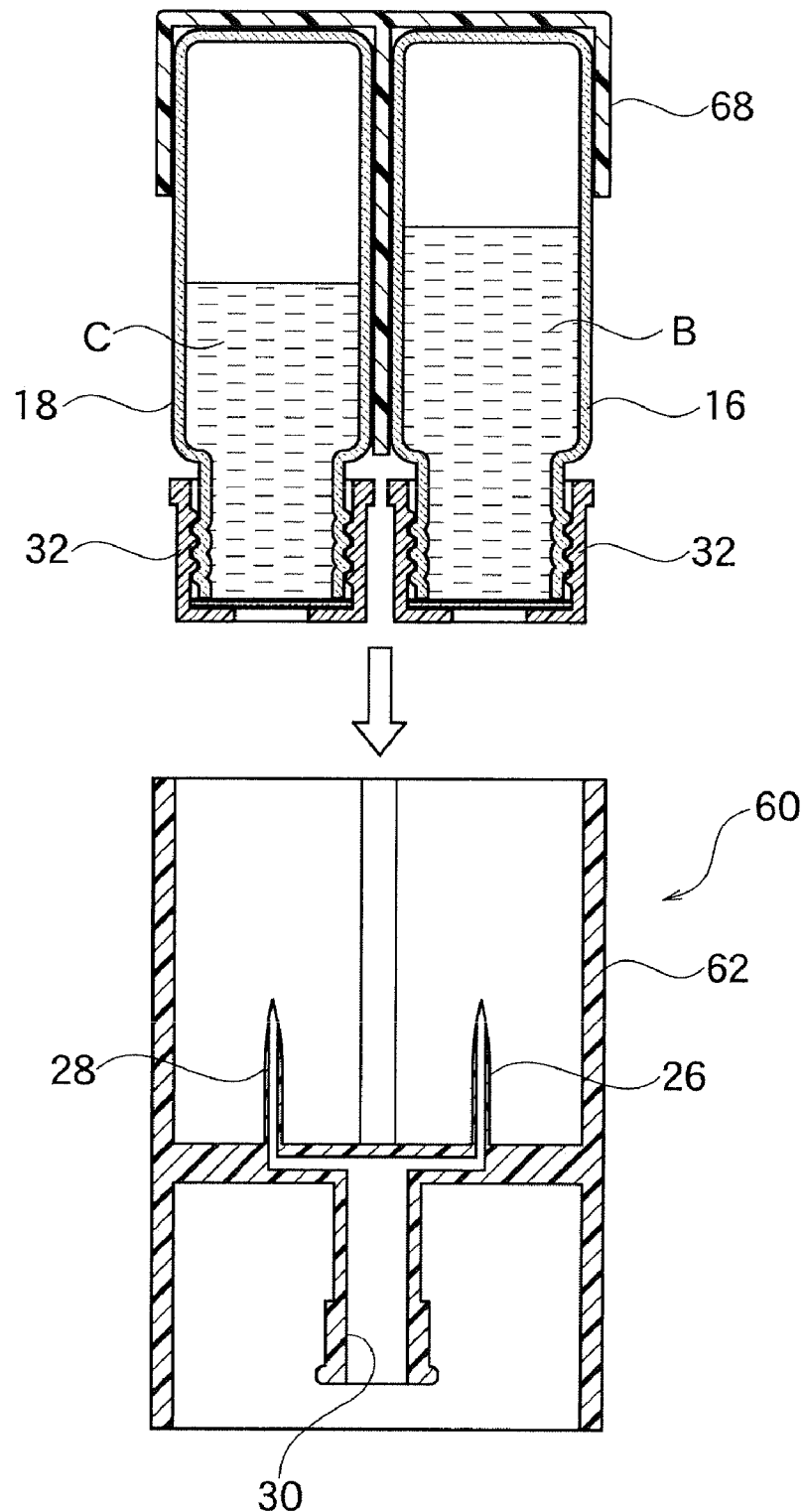

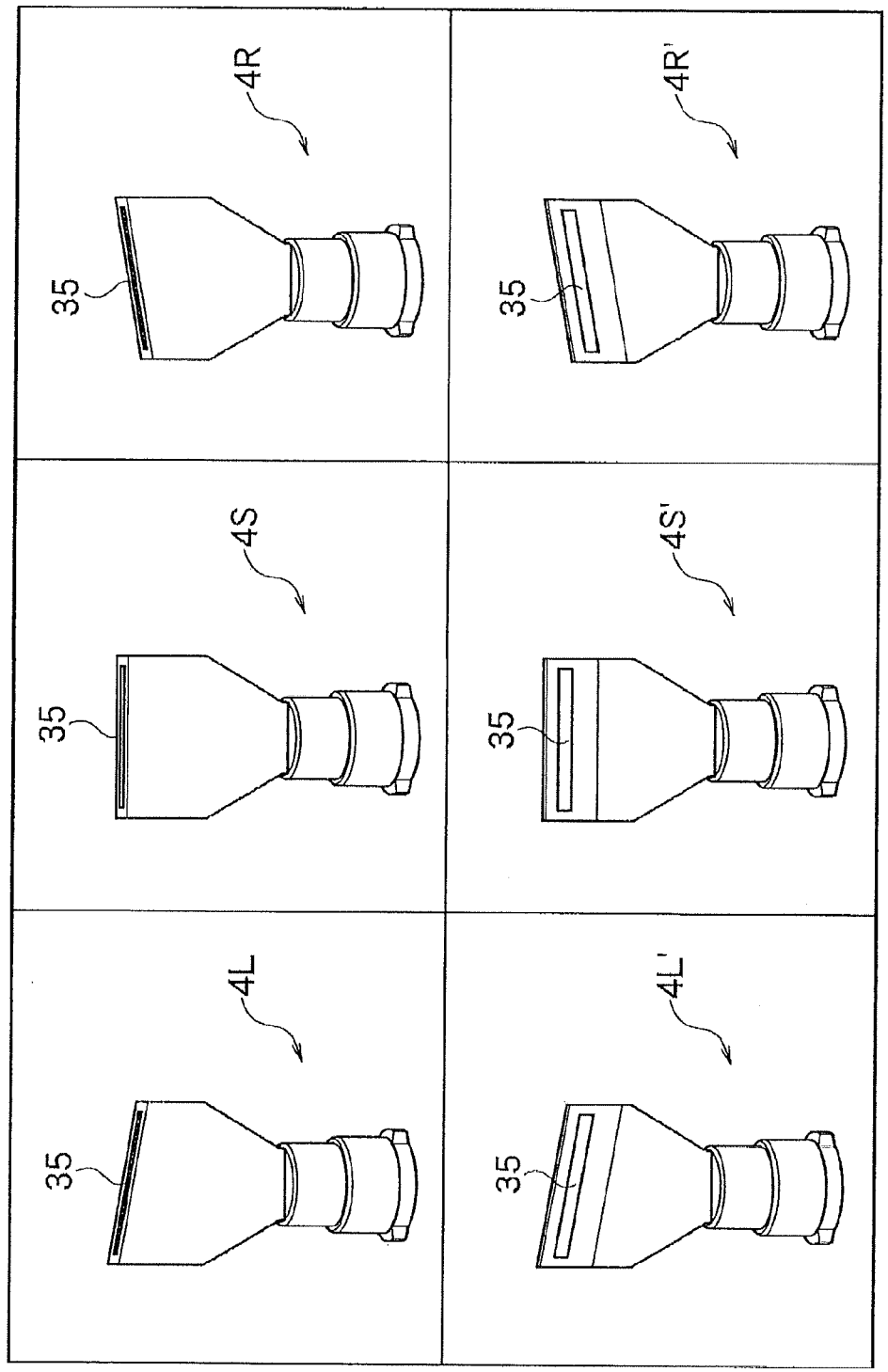
[Fig. 13]

[Fig. 14]
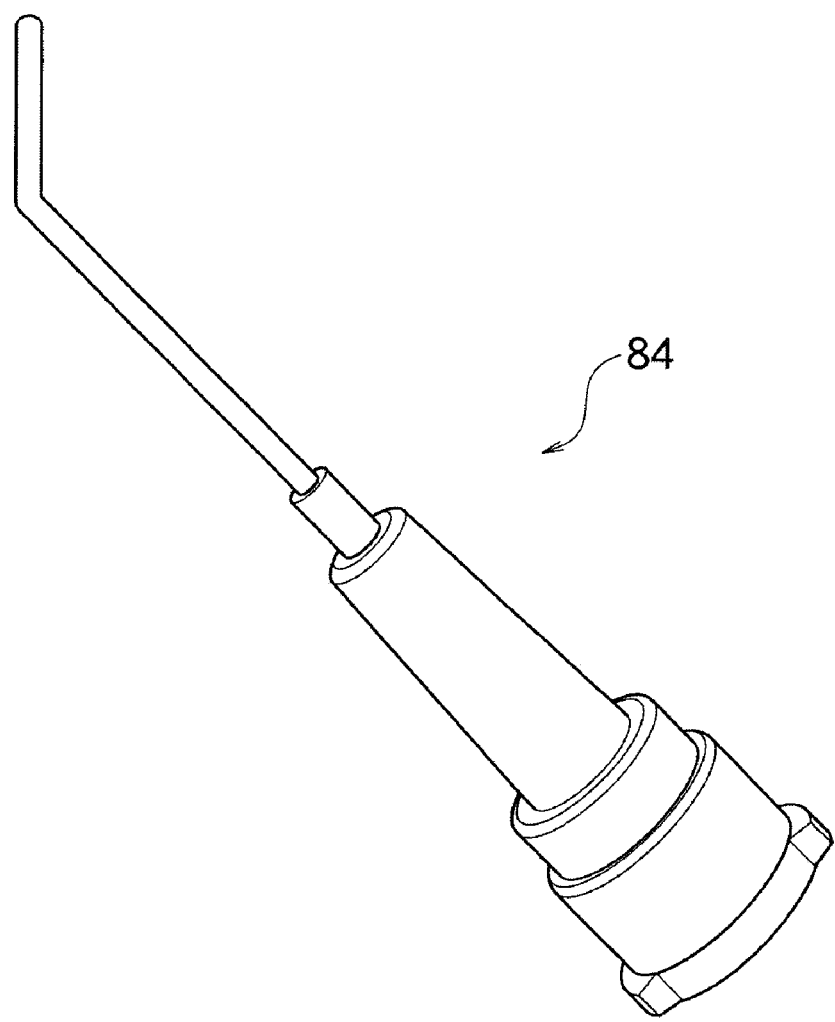

THREE-COMPONENT MIXING APPARATUS AND THREE-COMPONENT MIXING ADHESIVE KIT

TECHNICAL FIELD

The present invention relates to a three-component mixing apparatus and a three-component mixing adhesive kit suitable as a mixing container of a three-component mixing adhesive agent used in, for example, surgical procedure (or treatment) or dental procedure (or treatment).

BACKGROUND ART

In surgical procedure, for instance, suturing generally involves the use of suture thread. Suturing using suture thread, which is performed by someone's hands for long hours, cannot completely eliminate infection risk. In addition, since the surgical procedure leaves clear mark over a wide range, some surgical procedures have recently involved using adhesive agents in combination or singly. Using the adhesive agents to suture wound as described above can obviously reduce infection risk in operation and further improve esthetics after operation.

As the adhesive agent used in surgical procedure, two or more kinds of components are often mixed and used. Conventionally, such adhesive agents are used by introducing drugs in separate containers in advance, and then detaching a cap of a first component container and a cap of a second component container, and moving one drug of one component container to the other container. If a third drug is used, the third drug is generally added to the container in which the drugs of two kinds have been mixed. However, mixing three components as drugs in appropriate amount uniformly is cumbersome and is required to be improved.

An apparatus widespread for the mixing of a two-component mixing adhesive agent is disclosed in Patent Literature 1: with two components previously separately introduced in one syringe, a plunger is pressed to the syringe in use to mix the two components separated in the syringe.

Patent Literature 2 discloses a system configured to mix drugs by using an infusion-needle connector (container unit) capable of attaching two drug containers in parallel.

Although this mixing system employs the infusion-needle connector (container unit) capable of attaching two drug containers, since liquid is serially flown, transferring the whole liquid consumes much time.

CITATION LIST

Patent Literature

Patent Literature 1: JP-A-07-136264
Patent Literature 2: JP-A-2009-534144

SUMMARY OF INVENTION

Problems to be Solved by the Invention

The present invention has been made in consideration of such circumstances, and an object of the present invention is to provide a three-component mixing apparatus and a three-component mixing adhesive kit that allow anyone to easily and uniformly mix three kinds of drugs in a short period of time at the time of mixing a three-component adhesive used in, for example, surgical procedure (or treatment) or dental procedure (or treatment).

Means for Solving the Problems

The present invention has been made in order to solve the above-described problem.

A three-component mixing apparatus in accordance with the present invention comprises:

a syringe in which a discharge opening is formed on a leading end part and which has been filled with a first drug;

a plunger configured to be inserted into the syringe and in which a seal member is mounted; and an infusion-needle connector having a lead end part and a base end part, the lead end part including a connecting part for a second drug container filled with a second drug and a connecting part for a third drug container filled with a third drug, the base end part including a confluent path, wherein the apparatus is configured to mix the first drug, the second drug and the third drug in the syringe by attaching the second drug container to the connecting part for the second drug container, attaching the third drug container to the connecting part for the third drug container, and attaching the discharge opening of the syringe in a removable manner to the confluent path of the base end part of the infusion-needle connector; and then pulling the plunger against the syringe to introduce the second drug of the second drug container and the third drug of the third drug container into the syringe via the infusion-needle connector.

By the above configuration, three drugs can be mixed by pulling the plunger one time. Consequently, mixing operation can be easily performed in a short time.

In the three-component mixing apparatus in accordance with the present invention, it is preferable that a lubricant agent is applied on inner periphery of the syringe.

In the three-component mixing apparatus in accordance with the present invention moreover, it is preferable that a lubricant agent is applied on the seal member.

The lubricant agent is a substance that is applied on inner periphery of the syringe or on circumference of the seal member to improve slidability of the syringe and the seal member.

Examples of the lubricant agent are as follows.

Almond oil, esterified corn oil, epoxidized soybean oil, haze heating oil, olive oil, oleic acid, cacao butter, cacao powder, beef fat, beef fat hydrogenated oil, sesame oil, wheat germ oil, safflower oil, safflower oil fatty acid, labiatae oil, citronellal oil, snake oil, refined rice oil, soybean hydrogenated oil, soybean oil, soybean oil unsaponifiable matter, soybean lecithin, zinc oil, camellia oil, corn oil, No. 1-kerosene, kerosene, lard, canola oil, castor oil, sunflower seed oil, process oil, machine oil, mink oil, cotton seed oil, a mixture of cotton seed oil and soybean oil, coconut oil, arachis oil, egg yolk oil, rose oil, a copolymer solution of 2-ethylhexyl acrylate, 2-ethylhexy methacrylate, and dodecyl methacrylate, a copolymer resin emulsion of methyl acrylate and 2-ethylhexyl acrylate, an acrylic resin alkanolamine solution, di-isobutyl adipate, di-isopropyl adipate, a mixture of calcium alkyl allyl sulfonate and polyoxyethylene laurylether, alkyl allyl polyether alcohol, an alkyl sodium naphthalene sulfonate solution, a mixed emulsifier of alkylbenzene sulfonate and alkyl naphthalene sulfonate, a mixed emulsifier of alkylbenzene sulfonate, alkyl naphthalene sulfonate, and polyoxyethylene alkyl phenyl ether, an alkylbenzene sulfonate type emulsifier, alkylbenzene sulfonate powder, a mixed emulsifier of alkylbenzene sulfonate and polyoxyethylene alkyl ether, a mixed emulsifier of alkylbenzene sulfonate, polyoxyethylene alkyl ether, and fatty acid polyoxyethylene sorbitan, a mixed emulsifier of alkylbenzene sulfonate, polyoxyethylene alkyl ether, and polyoxyethylene alkyl phenyl ether, a mixed emulsifier of alkylbenzene sulfonate and polyoxyethylene alkylphenyl ether, a mixed emulsifier of alkylbenzene sulfonate and polyoxyethylene polycyclic phenyl ether, a mixed emulsifier of alkylbenzene sulfonate, polyoxyethylene alkyl phenyl ether, and polyoxyethylene alkyl allyl ether, a mixed emulsifier of alkylbenzene sulfonate and polyoxyethylene castor oil, alpha thioglycerin, a polymeric dibutyl phthalate solution of 4,4'-isopropylidene diphenol and 1-chloro-2,3-epoxypropane, isobornyl thio cyanoacetate, liquid lanolin, ethylene glycol, ethylene glycol ethyl ether, ethylene glycol monobutyl ether, ethylene glycol monomethyl ether, epoxy hexahydrophthalic diester, octyl phenoxy ethoxyethyl ether sodium sulfonate, guar gum, glycerin, glycerin fatty acid ester, gluconic acid, hydrogenated oil, synthetic scwaran, high glucose glutinous starch syrup, N-cocoyl-L-arginine ethyl esterDL-pyrrolidone carboxylic acid, N-cocoyl-N-methylaminoethyl sodium sulfonate, collodion, acidic phosphate isopropyl ester, diethanolamine, dipropylene glycol, sucrose fatty acid ester, silicon oil, silicone resin emulsion, a silicon antifoaming agent, hydrogenated vegetable oil, hydrogenated soybean phospholipid, scwaran, scwaren, refined soybean oil, refined honey, diisopropyl sebacate, sorbitan fatty acid ester, low substitution degree hydroxypropylcellulose, tocopherol, d-δ-tocopherol, triacetin, glycerin triiso octanoate, triethanolamine, a triethanolamine phosphate ester sodium solution, triethylene glycol, sorbitan trioleate, polyoxyethylene sorbitan trioleate (20E.O.), a mixture of tri(caprylic capric acid) glyceride and glyceride tristearate, tri(caprylic capric acid) glycerin, tris(nonylphenyl)phosphite, concentrated benzalkonium chloride solution 50, concentrated glycerin, honey, sodium hyaluronate, hydroxyethyl cellulose, hydroxyethyl methyl cellulose, N-hydroxyethyllactamide solution, hydroxylpropyl starch, hydroxylpropyl cellulose, hydroxylpropyl methyl cellulose 2208, hydroxylpropyl methyl cellulose 2906, hydroxylpropyl methyl cellulose 2910, hydroxylpropyl methyl cellulose acetate succinate, a mixture of hydroxylpropyl methyl cellulose 2910, titanium oxide, and macrogol 400, hydroxylpropyl methyl cellulose phthalate, piperonyl butoxide, phytic acid, diethyl phthalate, dioctyl phthalate, dibutyl phthalate, dimethyl phthalate, butyl phthalyl butyl glycolate, 1,3-butylene glycol, propylene glycol, propylene glycol fatty acid ester, 1,2,6-hexane triol, benzyl alcohol, polyacrylic acid, polyacrylic acid aqueous solution (20%), sodium polyacrylate, a polyacrylic acid partially neutralizing material, polyoxyethylene hydrogenated castor oil, polyoxyethylene hydrogenated castor oil 10, polyoxyethylene hydrogenated castor oil 100, polyoxyethylene hydrogenated castor oil 20, polyoxyethylene hydrogenated castor oil 40, polyoxyethylene hydrogenated castor oil 5, polyoxyethylene hydrogenated castor oil 50, polyoxyethylene hydrogenated castor oil 60, polyoxyethylene distyryl phenyl ether, polyoxyethylene sorbitan monolaurate, polyoxyethylene polycyclic phenyl ether ammonium sulfate acid, polyoxyethylene castor oil, polyoxyethylene (20) polyoxy propylene (20) glycol, polyoxyethylene (3) polyoxy propylene (17) glycol, polyoxyethylene coconut oil fatty acid glyceryl (7E.O.), polyoxyl 35 castor oil, polysorbate 20, polysorbate 40, polysorbate 60, polysorbate 65, polysorbate 80, polyvinyl alcohol (a partially saponifiable matter), a mixture of polyvinyl alcohol and diethylene glycol, a mixture of polyvinyl alcohol and dibutyl ether, polybutene, polypropylene glycol 2000, terminal hydroxyl substituted methyl polysiloxane silicone resin copolymer, myristic acid, isopropyl myristate, octyldodecyl myristate, lauryl methacrylate, α-monoisostearyl glyceryl ether, monoethanolamine, sorbitan monolaurate, polyethylene glycol monolaurate, lauryl diaminoethylglycine sodium solution, deca glyceryl laurate, a mixture of sulfated castor oil potassium salt and alkylbenzene sulfonate, fluid coumarone resin, polyoxyethylene oleyl ether phosphate (8MOL), royal jelly, copolymer dispersed liquid of ethyl acrylate and methyl methacrylate, isostearyl alcohol, isostearyl palmitate, isostearic acid, hexadecyl isostearate, octachloro dipropyl ether, octyl decyl triglyceride, octyl dodecanol, oleyl alcohol, ethyl oleate, oleyl oleate, decyl oleate, sodium oleate, xanthane gum, hydroxypropylcellulose including light anhydrous silicic acid, crystalline cellulose, crystalline cellulose carmellose sodium, crystalline cellulose (fine particle), crystalline cellulose (particle), a higher alcohol sulfated matter, a higher fatty acid salt type emulsifying agent, a mixed emulsifying agent of higher fatty acid salt and sulfated castor oil, synthetic aluminum silicate, hydroxypropyl starch, crystalline cellulose, highly refined egg yolk lecithin, wheat flour, wheat starch, wheat germ powder, rice powder, rice starch, white beeswax, ethylene glycol salicylate, starch oxide, diethylene glycol, diethylene glycol monobutyl ether, diethylene glycol monomethyl ether, dioctyl sodium sulfosuccinate, α-cyclodextrin, β-cyclodextrin, polyethylene glycol distearate, refined soybean lecithin, refined egg yolk lecithin, dextran, dextran 40, dextran 70, dextrin, palmitic acid, copolymer of n-butyl methacrylate and n-butyl acrylate, methacrylic acid copolymer L, methacrylic acid copolymerLD, methacrylic acid copolymer S, a mixed emulsifying agent of glycerin monoleate, glycerin dioleate, and propylene glycol, sorbitan monoleate, polyoxyethylene sorbitan monoleate (6E.O.), coconut oil fatty acid diethanolamide, lauryl alcohol, isopropyl linoleate, ethyl linoleate, acetyl glycerin fatty acid ester, isoparaffin, privet wax, castor wax, adsorptive purified lanolin, light liquid paraffin, whale wax, synthetic wax, hard wax, self-emulsification type propylene glycol stearate, self-emulsification type glyceryl monostearate, hydrogenated lanolin alcohol, stearyl alcohol, a mixture of stearyl alcohol and polyoxyethylene stearyl ether, stearic acid, zinc stearate, aluminum stearate, potassium stearate, calcium stearate, sodium stearate, polyoxyl 40 stearate, polyoxyl 45 stearate, polyoxyl 55 stearate, magnesium stearate, a mixed wax of refined paraffin and a carnauba wax, a refined montan wax, cetanol, a mixed wax of cetanol and polyoxyethylene cetyl ether, a mixed wax of cetanol, polyoxyethylene cetyl ether, and sodium lauryl sulfate, a mixed wax of cetanol and polysorbate 60, a mixed wax of cetanol and polyethylene glycol monostearate, a mixed wax of cetanol and polyoxyethylene sorbitan monostearate, cetostearyl alcohol, a mixture of cetostearyl alcohol and sodium cetostearyl sulfate, a mixture of cetostearyl alcohol and sodium lauryl sulfate, cetomacrogol 1000, polyoxyethylene glyceryl triisostearate, sorbitan tristearate, polyoxyethylene sorbitan tristearate, paraffin, a mixture of polyoxyethylene arachyl ether and stearyl alcohol, polyoxyethylene stearyl ether, polyoxyethylene stearyl ether phosphoric acid, polyoxyethylene cetyl ether, polyoxyethylene cetyl ether sodium phosphate, polyoxyethylene cetyl ether sodium phosphate (5E.O.), polyoxyethylene sorbit beeswax, polyoxyethylene nonylphenyl ether, a mixture of polyoxyethylene nonylphenyl ether and calcium alkylbenzene sulfonate, polyoxyethylene behenyl ether, polyoxyethylene (105) polyoxy propylene (5) glycol, polyoxyethylene (120) polyoxy propylene (40) glycol, polyoxyethylene (160) polyoxy propylene (30) glycol, polyoxyethylene (196) polyoxy propylene (67) glycol, polyoxyethylene (200) polyoxy propylene glycol (70), polyoxyethylene (1) polyoxy propylene (1) cetyl ether, polyoxyethylene (10) polyoxy propylene (4) cetyl ether, polyoxyethylene (17)

polyoxy propylene (23) cetyl ether, polyoxyethylene (20) polyoxy propylene (4) cetyl ether, polyoxyethylene (20) polyoxy propylene (8) cetyl ether, polyoxyethylene lanolin, macrogol 1000, macrogol 1500, macrogol 1540, macrogol 200, macrogol 20000, macrogol 300, macrogol 35000, macrogol 400, macrogol 4000, macrogol 600, macrogol 6000, beeswax, cetyl myristate, myristylmyristate, methyl myristate, Japan wax, polyethylene glycol monoleate, aluminum monostearate, ethylene glycol monostearate, glycerin monostearate, sorbitan monostearate, batyl monostearate, propylene glycol monostearate, polyethylene glycol monostearate, sorbitan nomopalmitate, glycerin monomyristate, polyoxyethylene sorbit monolaurate, coconut oil fatty acid, a mixture of sodium lauryl phosphate and glycerin monostearate, diethanolamide laurate, lauro macrogol, lanolin alcohol, lanolin fatty acid isopropyl, liquid paraffin, yellow petrolatum, hydrous lanolin, water adsorbable ointment (described with any one of A and B), hydrophilic ointment (described with any one of A and B), hydrophilic petrolatum (described with any one of A and B), lipophilic type glycerin monoleate, purified lanolin, simple ointment (described with any one of A and B), polyoxyethylene sorbit tetraoleate, white ointment (described with any one of A and B), white petrolatum, cetyl palmitate, polyoxyethylene alkyl ether, polyoxyethylene octylphenyl ether, polyoxyethylene oleylamine, polyoxyethylene oleyl ether, polyoxyethylene oleyl ether diethanolamine phosphate, polyoxyethylene oleyl ether sodium phosphate, polyoxyethylene (42) polyoxy propylene (67) glycol, polyoxyethylene (54) polyoxy propylene (39) glycol, polyoxyethylene lanolin alcohol ether (5E.O.), Macrogol ointment, glycerin monoleate, polyoxyethylene glycerin monostearate, polyoxyethylene sorbitan monostearate (6E.O.), polyoxyethylene laurylether sodium phosphate, petrolatum, a mixture of petrolatum and lanolin alcohol, a mixture of petrolatum, lanolin, and lanolin alcohol, starch acrylate 1000, starch acrylate 300, amylopectin, candy powder, pregelatinized starch, liquid sugar syrup, ethyl cellulose, ethyl cellulose aqueous dispersion, 2-cetyl ethylhexanoate, 2-etyl-1,3-hexanediol, carrageenan, caramel, karaya gum powder, carboxy vinyl polymer, carboxymethyl ethyl cellulose, carboxymethyl starch sodium, carmellose, carmellose potassium, carmellose calcium, carmellose sodium, reduced starch syrup, reduced maltose starch syrup, high fructose liquid sugar syrup, simple syrup, starch (soluble), starch ester sodium phosphate, potato starch, semi digestion starch, glucose fructose liquid sugar syrup, powder sugar, powder starch syrup, powder reduced maltose starch syrup, powder cellulose, pectin, starch syrup, and methyl cellulose.

The lubricant agent preferred is the one which is dissolved in either or both of the second drug and the third drug to reduce slidability of the seal member.

By the lubricant agent being dissolved in either or both of the second drug and the third drug after attaching the second drug container and the third drug container to the infusion-needle connector that has been attached to the syringe and then pulling the plunger to introduce the second drug and the third drug through the infusion-needle connector into the syringe, slidability of the seal member is reduced so that the plunger does not return to its original position even when the inside of the syringe is at a negative pressure state.

From such advantageous effects, the lubricant agents mentioned above are preferable examples. In particular, silicon oil can be mentioned as a more preferable example.

By using silicon oil as the lubricant agent, pulling the plunger in order to carry out the three-component mixing allows part of the silicon oil as the lubricant agent to be dissolved by drugs that come to be introduced into the syringe, resulting in the decrease of slidability of the plunger.

By the above configuration, suction force from the discharge opening side to be applied to the plunger would not cause the plunger to return to its original position. Consequently, the plunger can be stopped on its current position even when a hand is released from the plunger.

When silicon oil is applied as described above, pulling the plunger in order to carry out the three-component mixing allows part of the silicon oil to be dissolved by drugs that come to be introduced into the syringe. Meanwhile, silicon oil remaining on inner periphery of the syringe and the seal member as well as silicon oil on the side face of the seal member that has not come into contact with drugs introduced into the syringe keep enabling the plunger to be operated easily.

In the present invention, it is preferable that the connecting part for the second drug container and the connecting part for the third drug container, which are formed on the infusion-needle connector, are each provided with a needle member.

By the above configuration, attaching the second drug container and the third drug container to the connecting parts of the infusion-needle connector can be accompanied by forming holes on the drug containers.

In the present invention, it is preferable that the first drug is powder, the second drug is a liquid, and the third drug is a liquid.

By the above configuration where the first drug is powder, the second drug is a liquid and the third drug is a liquid, a user can mix and use the three components immediately.

A three-component mixing adhesive kit in accordance with the present invention comprises the three-component mixing apparatus as defined in any one of the above descriptions disassembled in a container box.

The above configuration is convenient for shipment, management and carrying around of the three-component mixing adhesive kit and for allowing a user to mix and use the three components immediately without making mistakes.

Advantageous Effects of Invention

By the three-component mixing apparatus in accordance with the present invention, three drugs can be mixed by one-time operation of pulling the plunger, so that three drugs in an appropriate amount can be easily and uniformly mixed with each other in a short time by anyone.

Furthermore, application of silicon oil on inner periphery of the syringe and the seal member, wherein the silicon oil as a lubricant agent is dissolved by drugs introduced into the syringe, reduces slidability of the plunger, so that the plunger can be prevented from returning to its original position even when a hand is released from the plunger during pulling the plunger. This configuration allows for easy stirring without the need for cumbersome operations such as stirring while holding the plunger.

Furthermore, when the infusion-needle connector is provided with needle members, attaching the drug containers can be accompanied by forming holes on the drug containers.

Furthermore, when the first drug is powder, the second drug is a liquid and the third drug is a liquid, the drugs can be effectively used for mixing of a surgical adhesive agent, a dental adhesive agent and so on. Consequently, a user such as a surgeon and a dentist, when needing an adhesive agent for a procedure or a treatment, can immediately mix and use three components as an adhesive agent on site.

Furthermore, by using a three-component mixing adhesive kit in accordance with the present invention, anyone can easily carry out a mixing operation without making mistakes.

BRIEF DESCRIPTION OF THE DRAWINGS

FIG. 1 is an exploded view showing an attaching mode when a three-component mixing apparatus and two drug containers in accordance with an embodiment of the present invention are attached to each other.

FIG. 2 is a schematic cross-sectional view showing a relationship between a three-component mixing apparatus in accordance with an embodiment of the present invention and a sealing member and a brush member that are selectively attached to the three-component mixing apparatus.

FIG. 3 is a perspective view showing an infusion-needle connector that is adopted for the three-component mixing apparatus in accordance with an embodiment of the present invention and a drug container that is attached to the infusion-needle connector.

FIG. 4 is a cross-sectional view showing an infusion-needle connector shown in FIG. 3.

FIG. 5 is a partially disassembled cross-sectional view showing separately a container body and a cap body of the drug container shown in FIG. 3.

FIG. 6 is a perspective view showing a three-component mixing adhesive kit in which each member of the three-component mixing apparatus in accordance with an embodiment of the present invention is contained in a container box.

FIG. 7 is a schematic cross-sectional view showing a state of the three-component mixing apparatus in accordance with an embodiment of the present invention before a mixing operation is carried out.

FIG. 8 is a perspective view showing a modified example of an infusion-needle connector.

FIG. 9 is a cross-sectional view showing a state in which a drug container is attached to the infusion-needle connector shown in FIG. 8.

FIGS. 10(A) and 10(B) are explanatory drawings showing another modified example of an infusion-needle connector and are explanatory drawings when a cylindrical member of the infusion-needle connector is extended and the two drug containers are attached to the infusion-needle connector by using a protrusion on inner periphery of the extended part.

FIG. 11 is an explanatory drawing when the two drug containers are attached to the infusion-needle connector by using a cap made of elastomer.

FIG. 12 is an explanatory drawing when the two drug containers are attached to the infusion-needle connector by using a collecting body.

FIG. 13 is a compendium showing examples of a variety of the brush member shown in FIG. 2.

FIG. 14 is a perspective view showing a nozzle in a pipe shape as substitute for the brush member shown in FIG. 13.

DESCRIPTION OF EMBODIMENTS

A three-component mixing apparatus in accordance with an embodiment of the present invention will be described below in detail with reference to the drawings.

FIG. 1 is an exploded view showing an attaching mode when a three-component mixing apparatus and two drug containers in accordance with an embodiment of the present invention are attached to each other. Such a three-component mixing apparatus 2 are employable to a wide variety of use applications as an apparatus configured to mix three components. In the following descriptions, however, an example that is applied to the mixing of an adhesive agent composed of three components will be described.

The three-component mixing apparatus 2 in accordance with the embodiment shown in FIG. 1 is provided with a syringe 4 in a cylindrical shape in which a first drug A is introduced in advance; a plunger 8 configured to be inserted into the syringe 4 and in which a seal member 6 is mounted on the leading end part; and an infusion-needle connector 10 that is attached to the outside of a discharge opening 4a of the syringe 4 in a removable manner. As described later, a second drug container 16 and a third drug container 18 are attached to the three-component mixing apparatus 2.

When the syringe 4 is filled with the first drug A, a sealing member 12 shown in FIG. 2 is attached to the discharge opening 4a of the syringe 4 in a removable manner. This configuration can prevent a drug or the like from leaking to the outside of the syringe 4. Consequently, it is preferable that the sealing member 12 is used from shipment until an operation of mixing drugs is carried out for instance. In FIG. 1, a symbol 4b is a plug part and a symbol 4c is an inner screw.

On the other hand, after three components are mixed by the three-component mixing apparatus 2 in a mode described later, when drugs that have been mixed are taken out as an adhesive agent, a brush member 14 shown in FIG. 2 is attached in place of the sealing member 12. In contrast to the sealing member 12, since the brush member 14 is internally provided with a path that leads up to the outside, the brush member 14 enables an adhesive agent to be applied or discharged.

In general, it is preferable that the plunger 8 is made of a polypropylene resin, although it varies depending on the type of a drug that configures an adhesive agent. Although not restricted in particular, it is preferable that the seal member 6 is made of a butyl-based rubber that is provided with chemical resistance (for instance, a butyl rubber and a chlorinated butyl rubber). Moreover, it is preferable that the seal member 6 is coated with silicon oil.

A connecting part 20 configured to attach a second drug container 16 and a connecting part 22 configured to attach a third drug container 18 are formed in parallel on the leading end part of the infusion-needle connector 10. On the other hand, a confluent path 30 is formed on a base end part of the infusion-needle connector 10. That is to say, in the infusion-needle connector 10 as shown in FIG. 4, two paths 26a and 28a are formed on one side, one confluent path 30 is formed on the other side, and the paths 26a and 28a and the confluent path 30 are connected to each other through bypass paths 26b and 28b.

As shown in FIG. 3, the connecting part 20 and the connecting part 22 that are formed in parallel in the infusion-needle connector 10 are provided with cylindrical skirt members 25 and 25 that have been halved by a slit 24 in a linear shape. This configuration enables the skirt members 25 to be slightly opened in an enlarged manner in a radial direction.

On the other hand, needle members 26 and 28 are protruded on the central part of the connecting part 20 and the connecting part 22 that are provided with the cylindrical skirt member 25, in which a through hole 34 is formed in the leading end part of the needle members 26 and 28.

It is preferable that the second drug container 16 and the third drug container 18 that are attached to the infusion-needle connector 10 in a removable manner have the same shape, whereby the same materials can be used for the two containers.

Since the second drug container 16 and the third drug container 18 have the same shape, the second drug container 16 will be described as an example in the following with reference to FIG. 5.

As shown in FIG. 5, the second drug container 16 is configured by a container body 16a and a cap body 32. In particular, it is preferable that the container body 16a is made of a glass with chemical resistance.

On the other hand, in the cap body 32 made of an appropriate synthetic resin, an aperture 32b is formed at the central part of a top board part 32a and a flange part 32c the diameter of which is slightly larger is formed on the lower end part. Since such a flange part 32c is formed on the lower end part of the cap body 32, when the second drug container 16 is inserted into the connecting part 20 of the infusion-needle connector 10, the cylindrical skirt member 25 is enlarged and opened.

Consequently, when the second drug container 16 with the cap body 32 mounted to the container body 16a is inserted into the connecting part 20 of the infusion-needle connector 10, and the flange part 32c of the cap body 32 passes through an aperture end of the connecting part 20, the cylindrical skirt member 25 is slightly enlarged and opened and captures the flange part 32c. Moreover, since restoring force to make the cylindrical skirt member 25 return to its original position is applied, the second drug container 16 can be held with certainty by the restoring force.

On the other hand as shown in FIG. 5, a seal member 37 is mounted on the reverse side of the top board part 32a of the cap body 32 in such a manner that the aperture 32b is covered.

The seal member 37 is provided with a three-layer structure. More specifically, the sealing member 37 is provided with a core material 37a made of a rubber member, more preferably a butyl-based rubber with high chemical resistance (for instance, a butyl rubber and a chlorinated butyl rubber), in the central part, and a fluorine resin film 37b such as Teflon (registered trademark) is bonded on the both sides of the core material 37a.

After the container bodies 16a, corresponding to the second drug container 16 and the third drug container 18, are filled with the second drug B and the third drug C, it is preferable that the entire outer periphery of the container body 16a and the cap body 32 (excluding the aperture 32b of the cap body 32) is covered with a shrink film.

When the entire outer periphery of the container body 16a and the cap body 32 is covered with a shrink film as described above, an inadvertent rotation of the cap body 32 can be prevented. This configuration can prevent the second drug B and the third drug C introduced inside from leaking outside.

As shown in FIG. 5, the second drug container 16 is attached to the connecting part 20 of the infusion-needle connector 10 in a removable manner and the third drug container 18 is attached to the connecting part 22 of the infusion-needle connector 10 in a removable manner. At this time, the needle members 26 and 28 protruded inside the infusion-needle connector 10 stick the seal member 37 of the second drug container 16 and the seal member 37 of the third drug container 18, respectively. At this time, holes each are opened in the seal members 37 and 37. Thereby, the second drug B and the third drug C in the container body 16a can be discharged outward.

The constituent elements of the three-component mixing apparatus in accordance with an embodiment of the present invention are formed as described above. It is preferable that the above constituent elements are packed in a container box 38 in an appropriate state as shown in FIG. 6 and are configured as a three-component mixing adhesive kit 50 and the three-component mixing adhesive kit 50 is shipped or managed in this state.

More specifically, the syringe 4 is filled with the first drug A, the plunger 8 is inserted into the syringe 4, and the sealing member 12 is attached to the discharge opening 4a of the syringe 4. As described above, a syringe assembly body 41 is configured by the syringe 4, the plunger 8 and the sealing member 12. In addition to the syringe assembly body 41, the second drug container 16 filled with the second drug B, the third drug container 18 filled with the third drug C, the infusion-needle connector 10 and the brush member 14 are packed in the container box 38.

After each of the constituent elements is packed in the container box 38 as described above, a sterilizing paper 42 is sealed on the upper opening of the container box 38 for shipment.

When the three-component mixing apparatus 2 is used for the mixing of an adhesive agent in surgical procedure (or treatment) or dental procedure (or treatment), the first drug A is a polymer (powder), the second drug B is a catalyst (liquid), and the third drug C is a monomer (liquid). In this case, as a polymer (powder) that is the first drug A, there can be mentioned for instance a powder made of a methacrylate polymer and a powder made of an acrylate polymer.

As a catalyst (liquid) that is the second drug B, there can be mentioned for instance an organic boron compound that is typified by trialkyl boron or the partial oxide thereof and a liquid in which an organic boron compound is dissolved in a solvent such as an aprotic solvent and a mixed solvent in which a small amount of alcohol is mixed to an aprotic solvent. As a monomer (liquid) that is the third drug C, there can be mentioned for instance methacrylate and acrylate that are typified by methyl methacrylate, ethyl methacrylate, butyl methacrylate, 2-hydroxyethyl methacrylate, 3-(trimethoxysilyl)propyl methacrylate, 2-(phenyl phosphoryl)ethyl methacrylate, 2-hydroxy-3-(β-naphthoxy)propyl methacrylate, N-phenyl-N-(2-hydroxy-3-methacryroxy)propyl glycine, ethylene glycol dimethacrylate, diethylene glycol dimethacrylate, triethylene glycol dimethacrylate, 1,4-butanediol dimethacrylate, 1,3-butanediol dimethacrylate, 2,2-bis[4-(2-hydroxy-3-methacryroxypropoxy)phenyl]propane, 2,2-bis(4-methacryroxyphenyl)propane, 2,2-bis(4-methacryroxyethoxyphenyl)propane, 2,2-bis(4-methacryroxypolyethoxyphenyl)propane, di(methacryroxyethyl) trimethylhexamethylene diurethane, trimethylolpropane trimethacrylate, hydroxylnaphthoxypropyl methacrylate, 4-methacryroxyethyl trimellitic anhydride, 4-methacryroxyethyl trimellitic acid, 11-methacryroxy-1,1-undecane dicarboxylic acid, 10-methacryroxy decamethylene phosphate, 4-methaacryloyl aminosalicylic acid, and 5-methaacryloyl aminosalicylic acid.

The usage when three components are mixed will be described next.

The syringe assembly body 41, the second drug container 16, the third drug container 18, and the infusion-needle connector 10 are taken out from the container box 38 for instance. First, the sealing member 12 is detached from the syringe assembly body 41. Then, the infusion-needle connector 10 is attached to the syringe assembly body 41, and the second drug container 16 and the third drug container 18 are then attached to the infusion-needle connector 10.

Through the above steps, the mixing of three components is ready as shown in FIG. 7.

In the meanwhile, it is also possible that the second drug container 16 and the third drug container 18 are attached to the infusion-needle connector 10 first and the infusion-needle connector 10 to which the second drug container 16 and the third drug container 18 have been attached is then attached to the syringe assembly body 41 from which the sealing member 12 has been detached.

As shown in FIG. 7, the plunger 8 is pulled down from the syringe 4 with the second drug container 16 and the third drug container 18 positioned on the upper side.

While an operation of pulling down of the plunger 8 from the syringe 4 is being carried out as described above, the second drug B in the second drug container 16 and the third drug C in the third drug container 18 can be sucked into the confluent path 30 through the bypass paths 26*b* and 28*b*, and can be introduced into the syringe 4.

The mixed drug of the second drug B and the third drug C that have been introduced into the syringe 4 is converged with the first drug A in the syringe 4. Even when a hand is released from the plunger 8 during the above operation, the plunger 8 does not return to its original position. This is because slidability of the plunger 8 is reduced as a result of part of the silicon oil applied on inner periphery of the syringe 4 and part of the silicon oil applied on the seal member 6 being dissolved in the second drug B and the third drug C introduced into the syringe 4.

When the second drug B and the third drug C are converged with the first drug A in the syringe 4 as described above, a kit assembly body 40 to which the infusion-needle connector 10 has been attached is shaken up and down in a hand in order to stir the drugs to rapidly complete uniform mixing.

When the mixing is completed, the infusion-needle connector 10 is detached and the brush member 14 shown in FIG. 2 is attached in place of the infusion-needle connector 10, whereby a preparation before use is completed.

After this preparation is completed, pushing the plunger 8 toward the discharge opening 4*a* can cause an adhesive agent desired to be discharged from the brush member 14 in appropriate amount. This enables applying the adhesive agent to, for example, surgical procedure (or treatment) or dental procedure (or treatment).

After use, the apparatus is put and collected into a container designed for waste disposal or the like and then discarded.

The three-component mixing apparatus 2 in accordance with an embodiment of the present invention can be effectively applied to the mixing of adhesive agents that would be hardened if the mixing of three components were not rapidly carried out. In addition, the operation is simple enough for anyone to carry out the operation without making mistakes.

When a large quantity of adhesive agent is used, using a plurality of three-component mixing apparatuses 2 or increasing a capacity of the syringe 4, the second drug container 16 and the third drug container 18 can provide specified quantity.

While the three-component mixing apparatus 2 in accordance with an embodiment of the present invention has been described above, the present invention is not restricted to the embodiment described above.

For instance, the infusion-needle connector 10 shown in FIGS. 3 and 4 may have other shapes. For example, in an infusion-needle connector 60 shown in FIG. 8, a wall body of the connecting part 20 and that of the connecting part 22 are formed in an integrated manner; the wall body is extended while having the same size to the outside of the confluent path 30; and protruding streaks 61, 61 and 61 for the frictional resistance are formed on the outer periphery of a cylindrical member 62 extended as described above.

In an infusion-needle connector 60 shown in FIG. 8, a plurality of protrusions 64 (three protrusions in FIG. 8) are formed on inner periphery of the connecting part 20 and the connecting part 22 separately at a predetermined interval.

The infusion-needle connector 60 configured as described above has a large area which contacts with a hand, and thus can be easily grasped by a user, which facilitates attaching of the drug containers and the stirring operation.

When a plurality of protrusions 64 are formed on inner periphery of the connecting part 20 and the connecting part 22, the following advantageous functional effects can be obtained.

That is to say, when the drug containers 16 and 18 are further inserted to the confluent path 30 side from their position shown in FIG. 9, moving the drug containers 16 and 18 over the protrusions 64 would require a larger pressing force compared to when the protrusions 64 are not formed.

In addition to the need for a larger pressing force, a user can experience force varied and sound generated when the drug containers 16 and 18 are moved over the protrusions 64 and sound made by hitting to a bottom face, thereby confirming whether or not the drug containers 16 and 18 have been inserted with absolute certainty.

When the drug containers 16 and 18 have been inserted with absolute certainty as described above, the protrusion 64 enters among a flange part 32*c* and the container body 16*a* of the drug containers 16 and 18 and a shoulder part of the container body 16*a*, thereby preventing the drug containers 16 and 18 from dropping out of the side of the confluent path 30.

Moreover, an infusion-needle connector 80 shown in FIGS. 10(A) and 10(B) can also be adopted.

The infusion-needle connector 80 is a modified example of the infusion-needle connector 60 shown in FIG. 8. For the infusion-needle connector 80, the cylindrical member 62 is further extended to form a skirt part 82. In a fixing part of the drug containers 16 and 18 in the skirt part 82, the slits 24 and 24 are formed in an axial direction. Moreover, a plurality of protrusions 64 and 65 is formed in a circumferential direction on inner periphery of the fixing part of the drug containers 16 and 18.

By forming a plurality of protrusions 65 as well as a plurality of protrusions 64 on inner periphery of the infusion-needle connector 80, the protrusions 65 enter between a flange part 32*c* and a shoulder part of the container body 16*a*, so that the cap bodies 32 and 32 of the drug containers 16 and 18 can be temporarily held and contained.

Thus, with the needle members 26 and 28 not yet inserted into the drug containers 16 and 18, the drug containers 16 and 18 can be temporarily fixed to the infusion-needle connector 80. Further inserting the drug containers 16 and 18 from their position shown in FIG. 10 would require a larger pressing force than ever before since the drug containers 16 and 18 are moved over the protrusions 64.

At the same time, the drug containers 16 and 18 are moved beyond the needle members 26 and 28 and fixed completely to the internal position, and the cap body 32 of the drug containers 16 and 18 comes into contact with the bottom face that is formed on the internal position of the skirt part 82. A user can feel force varied and sound generated when the drug containers 16 and 18 are moved over the protrusions 64 as well as sound generated by hitting to the bottom face, thereby confirming whether or not the drug containers 16 and 18 have been inserted with absolute certainty. When the drug containers 16 and 18 have been inserted with absolute certainty as described above, the protrusion 64 enters among the flange part 32c and the container body 16a of the drug containers 16 and 18 and a shoulder part of the container body 16a, thereby preventing the drug containers 16 and 18 from dropping out of the infusion-needle connector 80.

By this configuration, as shown in FIG. 6 for instance, when the constituent elements are packed in the container box 38 as the three-component mixing adhesive kit 50, it is also possible that the second drug container 16 and the third drug container 18 are temporarily fixed to the infusion-needle connector 80 and then shipped.

As shown in FIG. 11, when a cap 66 made of elastomer is prepared and the cap 66 is fitted to an aperture end of the infusion-needle connector 60 in appressed manner, for instance, the inside of the cap 66 enters between the flange part 32c and a shoulder part of the container body 16a, thereby temporarily fixing the drug containers 16 and 18 to the infusion-needle connector 60 or the like.

As shown in FIG. 12, when a collecting body 68 that can hold two drug containers 16 and 18 in parallel in a removable manner is prepared and the drug containers 16 and 18 are fixed to the collecting body 68 in advance, the drug containers 16 and 18 can be fixed to the infusion-needle connector 60 or the like by one-time operation. A material of the collecting body 68 can be any one of an elastomer and a synthetic resin.

The brush member 14 shown in FIG. 2 is not restricted to the embodiment described above.

As shown in FIG. 13, for instance, when a leading end face that forms a discharge part 35 of the brush member 14 is slanted, an adhesive agent can be applied easily.

In FIG. 13, the brush member 4S shows a standard form.

On the other hand, in the brush member 4S', the discharge part 35 is slanted at a predetermined angle.

In the brush members 4L' and 4R', the discharge part 35 is slanted at a predetermined angle similarly to the brush member 4S'.

In the brush members 4L and 4L', the discharge part is slanted in such a manner that a left end part is higher than a right end part as shown in FIG. 13. Consequently, the brush members 4L and 4L' are suitable for being used with a left hand.

In the brush members 4R and 4R', the discharge part is slanted in such a manner that a right end part is higher than a left end part as shown in FIG. 13. Consequently, the brush members 4R and 4R' are suitable for being used with a right hand.

Selecting an inclination angle of the brush member according to a dominant hand of a user as described above can improve the usability of the apparatus. When a small amount of an adhesive agent is used, a nozzle 84 with a pipe shape can also be used as shown in FIG. 14.

INDUSTRIAL APPLICABILITY

The present invention can be preferably utilized for the mixing of adhesive agents that are used in surgical procedure (or treatment) or dental procedure (or treatment). In addition, the present invention can also be applied to the mixing of adhesive agents of dental materials or the mixing of adhesive agents of industrial products.

Moreover, the present invention can also be effectively applied to the mixing of three components other than adhesive agents. In particular, the present invention is effective when three components are mixed in a short time.

REFERENCE SIGNS LIST

2: Three-component mixing apparatus
4: Syringe
4a: Discharge opening
4b: Plug part
4c: Inner screw
6: Seal member
8: Plunger
10: Infusion-needle connector
12: Sealing member
14: Brush member
16: Second drug container
16a: Container body
18: Third drug container
20: Connecting part
22: Connecting part
24: Slit
25: Cylindrical skirt member
26: Needle member
26a: Path
26b: Bypass path
28: Needle member
28a: Path
28b: Bypass path
30: Confluent path
32: Cap body
32a: Top board part
32b: Aperture
32c: Flange part
34: Through hole
35: Discharge part
37: Seal member
37a: Core material
37b: Fluorine resin film
38: Container box
40: Kit assembly body
41: Syringe assembly body
42: Sterilizing paper
50: Three-component mixing adhesive kit
60: Infusion-needle connector
61: Protruding streak
62: Cylindrical member
64: Protrusion
66: Cap
68: Collecting body
80: Infusion-needle connector
82: Skirt part
84: Nozzle
A: First drug
B: Second drug
C: Third drug

The invention claimed is:

1. A three-component mixing apparatus comprising:
a first drug, a second drug and a third drug;
a syringe in which a discharge opening is formed on a leading end part and which contains said first drug;
a plunger configured to be inserted into the syringe and in which a seal member is mounted;
a second drug container composed of a container body containing said second drug and a cap body attached to an opening of the container body and having a circumferential flange in a lower end thereof;

a third drug container composed of a container body containing said third drug and a cap body attached to an opening of the container body and of the third drug container having a circumferential flange in a lower end thereof; and an infusion-needle connector having a lead end part and a base end part, the lead end part including a connecting part for the second drug container filled with said second drug and a connecting part for the third drug container filled with said third drug, the base end part including a confluent path, wherein the apparatus is configured to mix said first drug, said second drug and said third drug in the syringe by attaching the second drug container to the connecting part for the second drug container, attaching the third drug container to the connecting part for the third drug container, and attaching the discharge opening of the syringe in a removable manner to the confluent path of the base end part of the infusion-needle connector; and then pulling the plunger against the syringe to introduce said second drug of the second drug container and said third drug of the third drug container into the syringe via the infusion-needle connector, and wherein a plurality of protrusions over which the circumferential flange of the second drug container and the circumferential flange of the third drug container are moved are formed on an inner periphery of the connecting parts separately at a predetermined interval to allow the second drug container and the third drug container with the respective cap bodies on to move linearly without being rotated over the protrusions and be inserted.

2. The three-component mixing apparatus as defined in claim 1, wherein a lubricant agent is applied on an inner periphery of the syringe.

3. The three-component mixing apparatus as defined in claim 1, wherein a lubricant agent is applied on the seal member.

4. The three-component mixing apparatus as defined in claim 2, wherein the lubricant agent is silicon oil.

5. The three-component mixing apparatus as defined in claim 1, wherein the connecting part for the second drug container and the connecting part for the third drug container that are formed on the infusion-needle connector are each provided with a needle member.

6. The three-component mixing apparatus as defined in claim 1, wherein said first drug is powder, said second drug is a liquid, and said third drug is a liquid.

7. A three-component mixing adhesive kit comprising the three-component mixing apparatus as defined in claim 1, disassembled in a container box.

8. The three-component mixing apparatus as defined in claim 3, wherein the lubricant agent is silicon oil.

* * * * *